United States Patent
Guba et al.

(10) Patent No.: US 9,757,138 B2
(45) Date of Patent: Sep. 12, 2017

(54) INSTRUMENT WITH IMPROVED TOOL

(71) Applicant: ERBE Elektromedizin GmbH, Tuebingen (DE)

(72) Inventors: Joachim Guba, Weil der Stadt (DE); Lothar Mitzlaff, Lagos (PT); Ralf Kuehner, Stuttgart (DE); Martina Heim, Pliezhausen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 343 days.

(21) Appl. No.: 14/479,013

(22) Filed: Sep. 5, 2014

(65) Prior Publication Data
US 2015/0073451 A1 Mar. 12, 2015

(30) Foreign Application Priority Data

Sep. 10, 2013 (EP) .................................. 13183633
Sep. 12, 2013 (EP) .................................. 13184189

(51) Int. Cl.
*A61B 17/285* (2006.01)
*A61B 17/28* (2006.01)
(Continued)

(52) U.S. Cl.
CPC ........ *A61B 17/2816* (2013.01); *A61B 17/285* (2013.01); *A61B 17/2833* (2013.01);
(Continued)

(58) Field of Classification Search
CPC .......... A61B 18/085; A61B 2018/0063; A61B 2018/00601; A61B 2018/00589;
(Continued)

(56) References Cited

U.S. PATENT DOCUMENTS 6,585,735 B1   7/2003   Frazier et al.
6,818,007 B1 *   11/2004   Dampney .............. A61B 17/29
    606/205
(Continued)

FOREIGN PATENT DOCUMENTS

CN         101779979 B     1/2013
DE   202007009165 U1   10/2007
(Continued)

OTHER PUBLICATIONS

Office action in corresponding Korean Application No. 2014-0120483, dated Dec. 17, 2015, 15 pages.
(Continued)

*Primary Examiner* — Joseph Stoklosa
*Assistant Examiner* — Jennifer Le
(74) *Attorney, Agent, or Firm* — Fitch, Even, Tabin & Flannery LLP

(57) ABSTRACT

An instrument (10) having a tool (15) of a particularly simple design comprises jaws (16, 17) with jaw supports (46) supported by spaced-apart hinges on a shared socket part 18. The hinge axes (27, 28) of the hinges are oriented parallel relative to each other and are at a distance from each other. A slit (24) for precisely guiding a knife (25) may be provided between the two. The jaw supports (46) of the jaws (16, 17) are guided in their own hinges with minimal play and hence in a precise manner. They are held against each other by transverse interlocking means (37), thereby ensuring a simple assembly and precise guiding.

15 Claims, 3 Drawing Sheets

(51) Int. Cl.
  *A61B 17/29* (2006.01)
  *A61B 18/14* (2006.01)
  *A61B 18/00* (2006.01)
  *A61B 90/00* (2016.01)

(52) U.S. Cl.
  CPC .. *A61B 18/1445* (2013.01); *A61B 2017/2939* (2013.01); *A61B 2017/2947* (2013.01); *A61B 2018/0063* (2013.01); *A61B 2018/1455* (2013.01); *A61B 2090/035* (2016.02)

(58) Field of Classification Search
  CPC ..... A61B 17/28; A61B 17/2804; A61B 17/29; A61B 2017/2926
  USPC .......................................................... 606/51
  See application file for complete search history.

(56) References Cited

U.S. PATENT DOCUMENTS

| | | | |
|---|---|---|---|
| 7,131,977 B2* | 11/2006 | Fowler | A61B 17/1285 606/138 |
| 2002/0143358 A1 | 10/2002 | Domingo et al. | |
| 2003/0199869 A1 | 10/2003 | Johnson et al. | |
| 2003/0216733 A1 | 11/2003 | McClurken et al. | |
| 2004/0044363 A1 | 3/2004 | Fowler | |
| 2011/0054468 A1 | 3/2011 | Dycus | |
| 2011/0251613 A1* | 10/2011 | Guerra | A61B 17/295 606/52 |
| 2012/0283734 A1 | 11/2012 | Ourada | |
| 2013/0046295 A1 | 2/2013 | Kerr et al. | |
| 2013/0085516 A1 | 4/2013 | Kerr et al. | |

FOREIGN PATENT DOCUMENTS

| | | |
|---|---|---|
| DE | 102006062848 B4 | 1/2013 |
| JP | 2003509104 A | 3/2003 |
| JP | 2004516043 A | 6/2004 |
| WO | 2008040483 A1 | 4/2008 |
| WO | 2009003575 A1 | 1/2009 |

OTHER PUBLICATIONS

Office action and Search report in corresponding Japanese Application No. 2014-184575, dated Jan. 21, 2016, 43 pages.
Office action in corresponding Russian Application No. 2014136538, 6 pages.
European Search Report for corresponding application EP13184189.2, dated Jan. 3, 2014.
European Search Report for corresponding application EP13184189.2, dated Mar. 11, 2014.

* cited by examiner

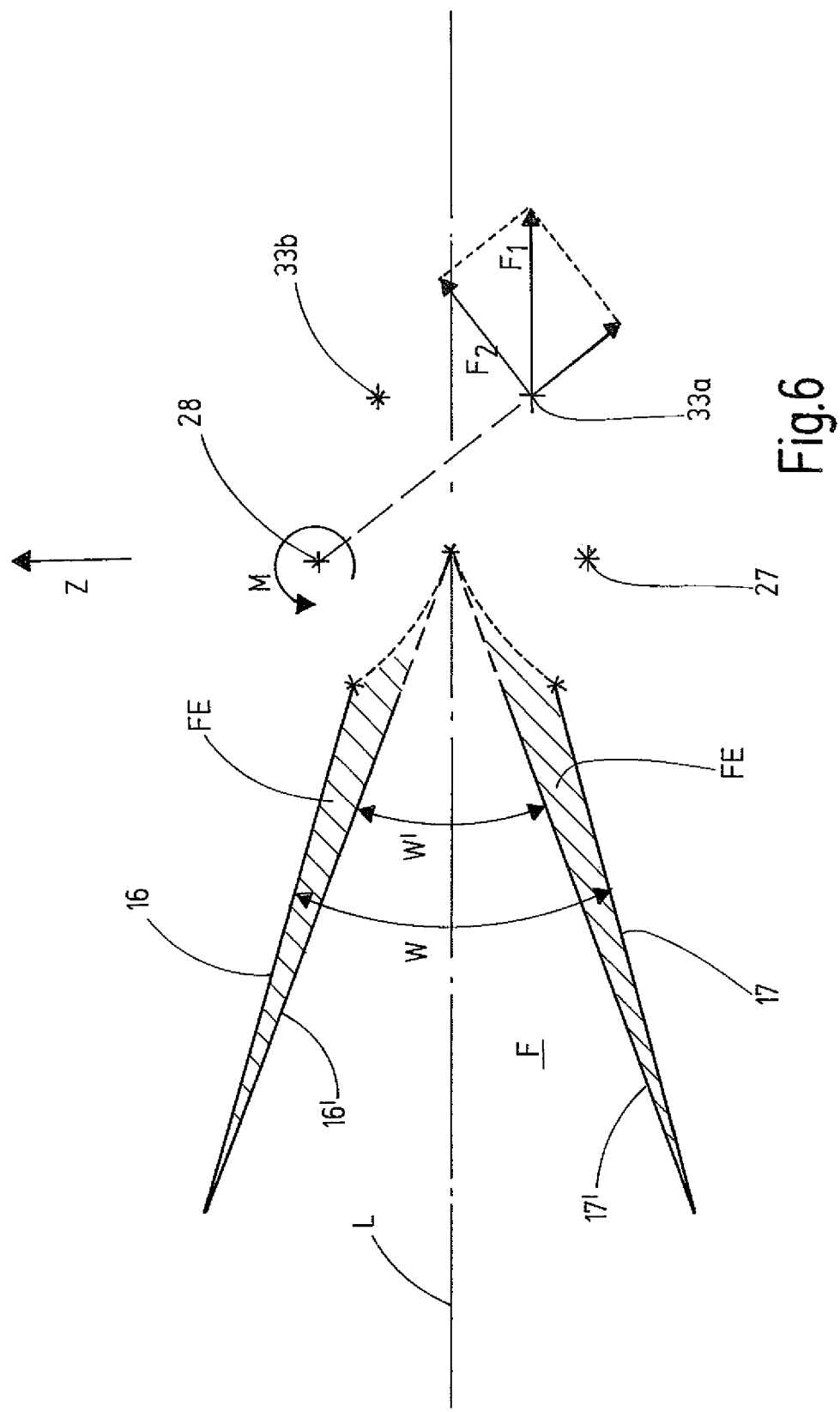

INSTRUMENT WITH IMPROVED TOOL

RELATED APPLICATION(S)

This application claims the benefit of European Patent Application No. EP13183633.0 filed Sep. 10, 2013 and European Patent Application No. EP13184189.2 filed Sep. 12, 2013, the contents of each of which are incorporated herein by reference as if fully rewritten herein.

TECHNICAL FIELD

The invention relates to a surgical instrument, in particular a coagulation instrument or an instrument for sealing vessels with the use of a tool, said tool comprising two movable jaws.

BACKGROUND

Hereinafter, the term "distal" always describes the part of the instrument or component remote from the user, and the term "proximal" always describes the part of the instrument or component directed toward and being closer to the user.

An instrument having the aforementioned design has been known from publication US 2011/0054468 A1. The instrument illustrated there comprises two jaws that are pivotally supported by the distal end of a shaft, said jaws having a shared pivot bearing. The pivot bearing defines a hinge axis extending transversely to the shaft. In addition, a longitudinally movable knife is provided, whereby said knife can be slid in distal direction when the jaws are closed in order to sever a clamped-off and coagulated vessel.

Publication US 2003/0199869 A1 discloses a similar instrument comprising two jaws that are supported so as to be pivotable about a shared hinge axis. The jaws support the electrodes for the coagulation of a vessel. Again, a knife is provided that can be moved in distal direction between the closed jaws in order to sever a coagulated and sealed tissue bundle.

An instrument in accordance with at least one of the embodiments of publication DE 20 2007 009 165 U1 has a similar design.

In all the mentioned designs the arrangement of the hinge region with the hinge axes and the knife extending through this hinge region are fraught with problems.

SUMMARY

Considering this, it is the object of the invention to provide an instrument wherein the two jaws and, if present, the knife is guided with great precision.

The surgical instrument in accordance with the invention comprises a tool with two pivotally supported jaws. Preferably, each jaw consists of a jaw support and electrode units affixed thereto. In doing so, the jaw supports are disposed for the transmission of mechanical forces and for the support of the jaws. Both jaw supports are held by a socket part on various, spaced-apart hinges so as to be pivotable toward each other and away from each other. Due to the spatial distance between the two hinges and their hinge axes relative to each other, a knife may be arranged and supported between these.

The distance between the two hinges makes it possible the to more precisely guide the pivoting motion of each of the jaws by increasing the length of the hinge axes or their axial guide length, compared to a shared hinge axis. The axial guide length may take up more than half the width of the tool or the diameter of the shaft. In doing so, the width is measured in the direction of the hinge axis, i.e., transversely to the shaft. Additionally, the distance between the hinge axes makes it possible that, with the jaws opened, an enlarged tissue receiving range is available. Furthermore, if the hinge axes are at a distance from each other, the relationships regarding the force required for closing the jaws will change. This allows greater closing forces that contribute to an improved holding of the tissue and to improved vessel sealing.

In addition, the distance created between the two hinges can be used to provide room for a passage for a knife. Consequently, this knife does not extend through any of the hinge axes. Furthermore, a slit may be provided in the socket part for guiding this knife, said slit creating the breakthrough for the knife and assuming part of the guiding operation or the support of the knife, thereby improving such guiding and support.

Considering the design of the mentioned hinges, a bearing pin on one part and a bearing bushing on another part are used. Preferably, the bearing pin comprises a cylindrical bearing section connected to a fillet. The bearing bushing on the other part comprises a matching, preferably cylindrical, section with an opening. In one embodiment, the bearing bushing is arranged in the socket part and the bearing pin is arranged on the jaw support of the jaw. In another embodiment, the association may be reversed.

The bearing pin in the form of a bearing section with fillet is preferably seamlessly configured in one piece along a strip-shaped necked-in region along its generated surface with the jaw support. In addition, the bearing pin may terminate on one end side in the branch support. In this manner, a robust and precise hinge is being formed together with the complementarily shaped bearing bushing in the socket part. In addition, the hinge is easy to mount in that the bearing pin is axially inserted in the bearing bushing that is open on one end.

The opening of the bearing bushing has a width that is smaller than the diameter of the cylindrical bearing section of the bearing pin. However, the width of the opening is slightly greater than the fillet of the bearing pin that connects the bearing section to the jaw support, so that a pivoting motion of the jaw support relative to the socket part is possible.

Preferably, the socket part is made of plastic material. The jaw support may be made of plastic material, ceramic material, composite material or metal. The jaw supports may support electrode units that consist of a body of plastic material with a metal inlay. These metal inlays may be sheet metal parts that act as electrodes or as tissue contact surfaces and are electrically and thermally insulated with respect to the jaw supports due to the plastic material body. In doing so, the coagulation effects are restricted to the tissue clamped between the two jaws of the tool.

A particularly simple assembly of the tool is made possible if the jaw supports are provided with transverse interlock means. These lock the jaw support in the direction of the hinge axes, i.e., transversely to the tool. Such transverse interlocking means may be projections or ribs and recesses or pockets provided on the jaw supports and extending in circumferential direction, said means coming into engagement with each other in closed and normally opened state of the tool. The attachment of the jaw supports to the socket part is performed in an assembly position in that the bearing pins of the jaw supports are inserted in opposite directions in the bearing bushings of the socket part, these being parallel to each other, and are then pivoted onto each other in such a manner that, respectively, one rib of one jaw support comes into engagement with the matching pocket of the other jaw support. In order to accomplish this, it is advantageous if the pockets and the ribs are offset in lateral direction (axially relative to the hinge axis) as well as in circumferential direction.

Additional advantageous details of embodiments of the invention can be inferred from the description or the claims and the drawings.

BRIEF DESCRIPTION OF THE DRAWINGS

FIG. 6 the grasping range of a tool 15 according to the invention.

DETAILED DESCRIPTION

Figure 1:
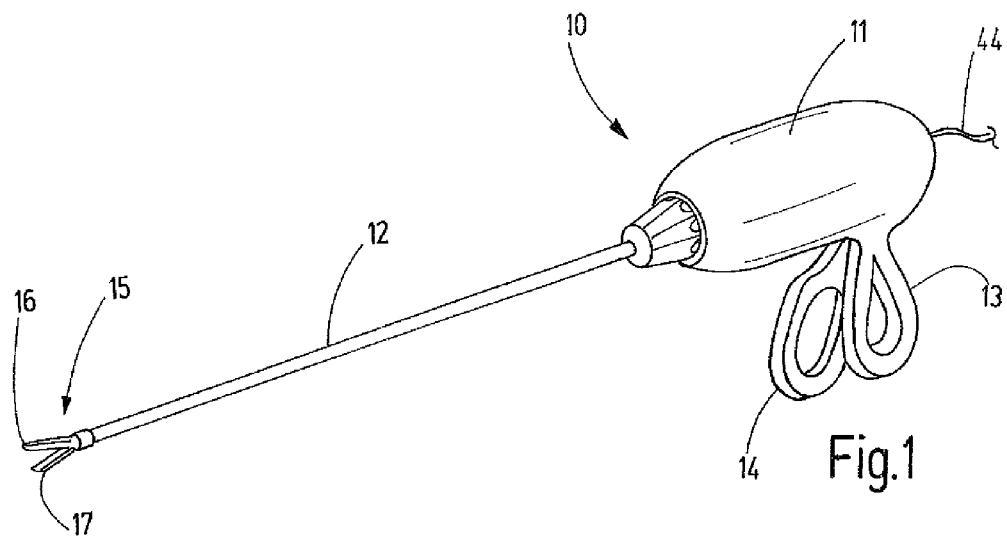
FIG. 1 an instrument according to the invention, in a schematized perspective representation.

FIG. 1 shows a surgical instrument 10, said instrument being disposed for vessel sealing in open surgery. The instrument 10 comprises a housing 11 from which extends a preferably straight shaft 12. Provided on the housing 11 is a handle 13 adjacent to which a control lever 14 is supported so as to be pivotable. The control lever 14 is disposed for actuating a tool 15 affixed to the distal end of the shaft 12. The instrument 10 may be configured as a disposable instrument and be intended for single use only. However, it may also be configured as a sterilizable and thus reusable instrument.

Figure 2:
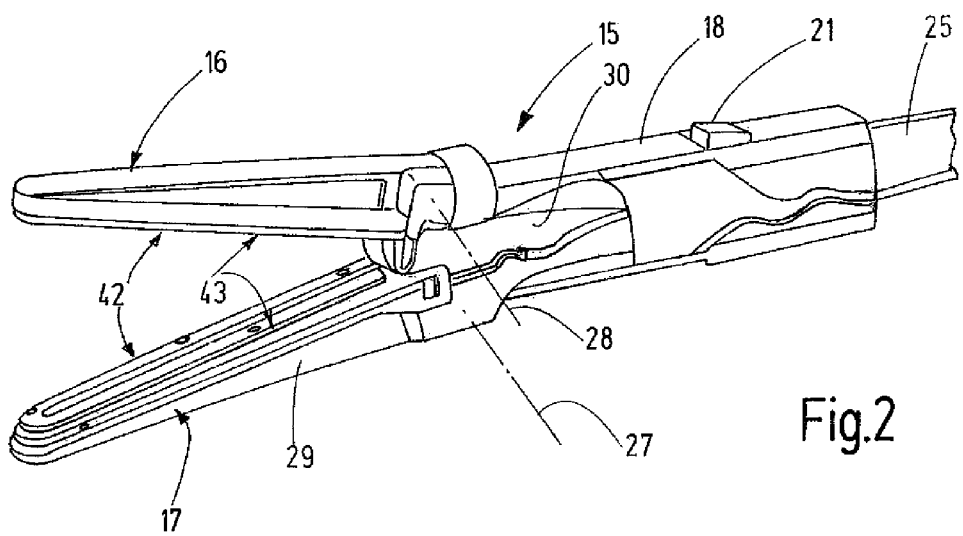
FIG. 2 a tool of the instrument as in FIG. 1 with two jaws and the socket part, in a schematized perspective representation.
Figure 3:
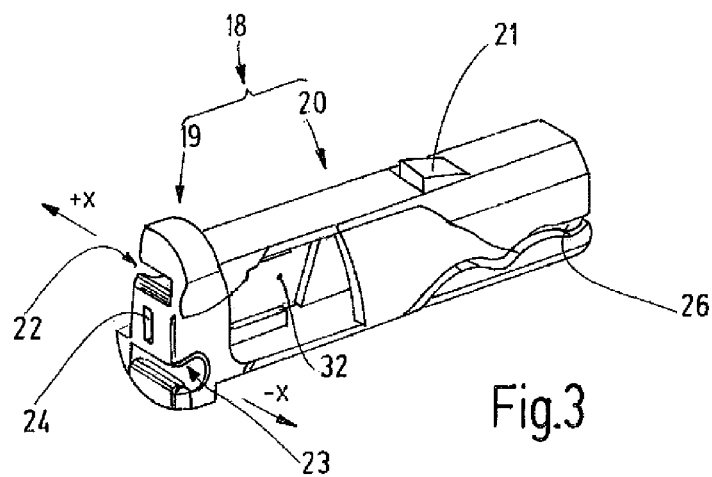
FIG. 3 a socket part of the tool as in FIG. 2, in a separate perspective representation.

The special feature of the instrument 10 is the configuration of the tool 15 shown separately by FIG. 2. The tool 15 comprises a first and a second jaw 16, 17, both of them being movably supported by a socket part 18. The socket part 18 may consist of plastic material, ceramic material, composite material or also of metal, for example. FIG. 3 shows the socket part 18 by itself. Said socket part comprises a distal support section 19 and an extension 20 extending therefrom. The extension 20 is inserted in the distal end of the shaft 12 and, for example, interlocked therewith by means of a detent 21. In the distal support section 19, two bearing bushings 22, 23 that are parallel relative to each other and open toward different flanks and undercut are provided, said bearing bushings extending in transverse direction +X or –X and, furthermore, being open toward the distal end of the socket part 18. Between the two bearing bushings 22, 23 there may be provided a slit 24 through which a knife 25 may be slid for severing coagulated tissue, in particular sealed vessels.

The extension 20 that is hollow on the inside may have on the outside of its two flanks corrugated grooves 26 for receiving electrical lines that are disposed to provide the jaws 16, 17 with a voltage or current. The corrugated grooves 26 accommodate the corresponding electrical lines in a stretch-resistant manner and thus act as a strain relief for said lines. The strain relief of the electrical lines may also be accomplished with differently configured positive-locking means such as, for example, pin or fillet arrangements that are offset relative to each other.

Figure 4:
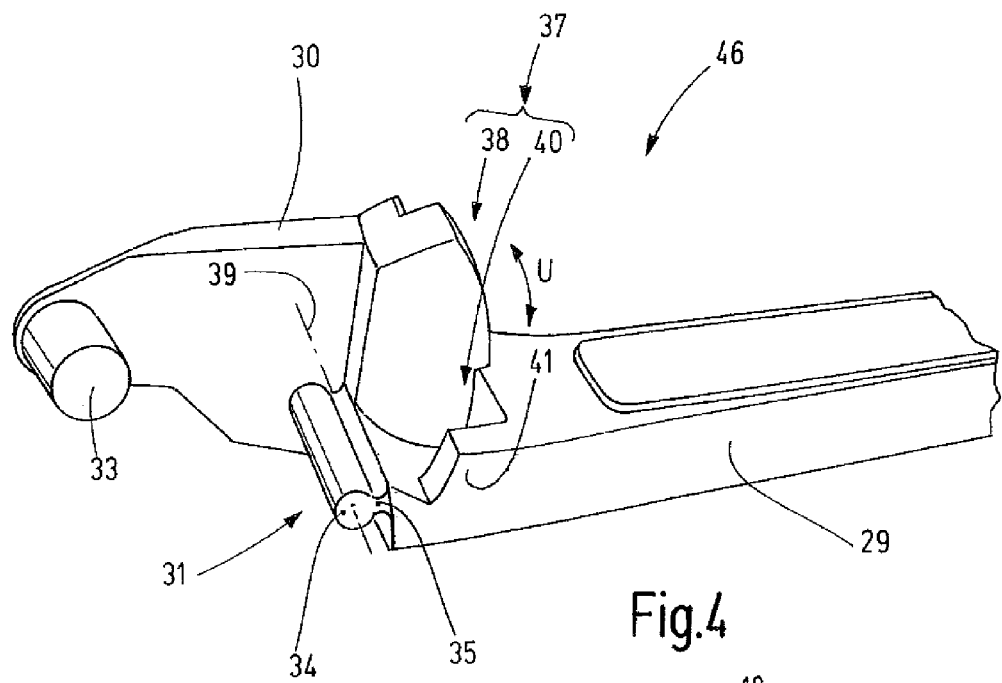
FIG. 4 a jaw support of a jaw of the tool as in FIG. 2, in a separate perspective representation of a detail.

Each of the jaws 16, 17 comprises a jaw support 46 as shown by FIG. 4. As has already been indicated in FIG. 2, the two jaws 16, 17 are supported by the socket part 18 about two parallel, spaced-apart hinge axes 27, 28. The corresponding hinges are represented, respectively, by structures of the socket part 18, as well as of the jaw support 46 of the jaw 16, 17.

The explanation of the jaw support 46 of a first jaw 16 applies, correspondingly, to the preferably complementarily configured second jaw 17.

Figure 5:
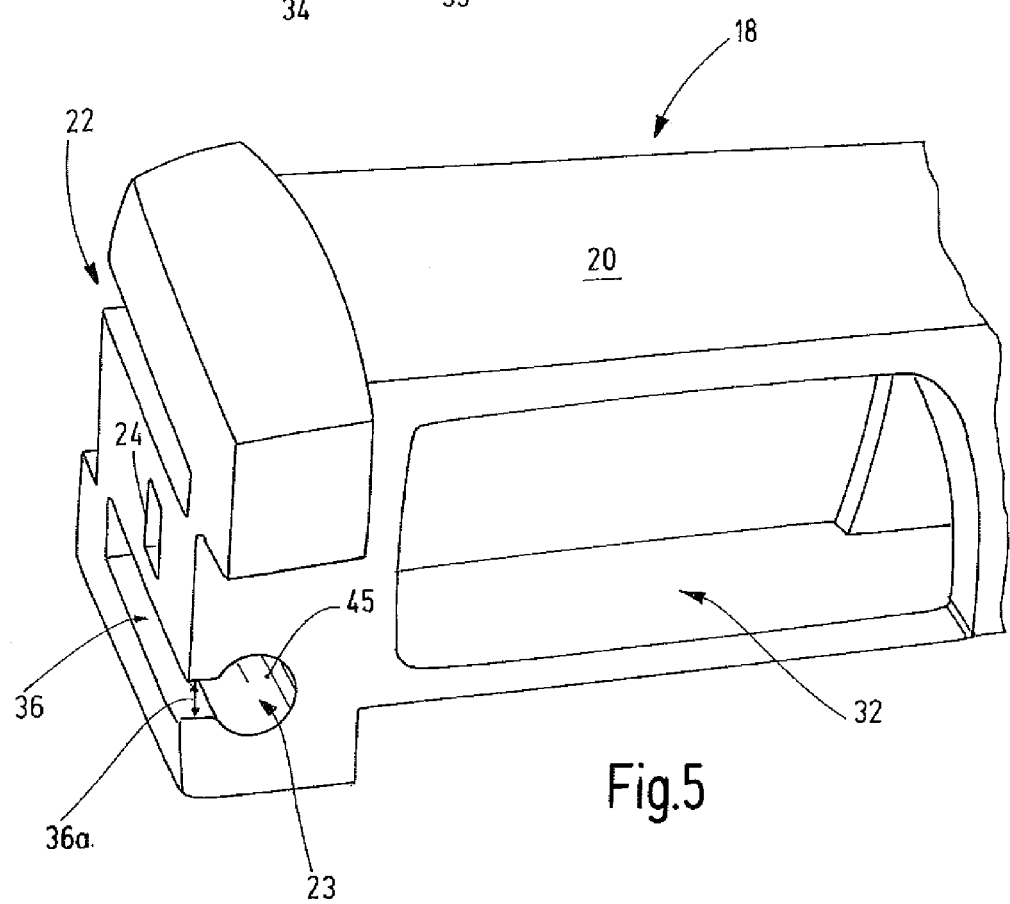
FIG. 5 the socket part as in FIG. 3, in a larger perspective representation of a detail.

The hinge defining the hinge axis 27 is formed between the jaw support 46 and the socket part 18, these being shown separately in FIGS. 4 and 5. The jaw support 46 consisting of plastic material, ceramic material, composite material or metal is preferably configured in one piece and without seams. Extending in distal direction, there is a tool member 29 that terminates on its rear end in an eccentrically positioned actuating member 30 as well as a bearing pin 31. The actuating member 30 fits into a recess with a window 32 provided laterally on the socket part 18 (FIG. 3, FIG. 5). An inward-directed actuating pin 33 provided on the actuating member 30 may be—in the interior space of the extension 20—in connection with the pull-push means for a pivoting actuation of the jaw support 46 of the first jaw 16. The same applies to the second jaw 17.

The bearing pin 31 comprises a preferably cylindrical bearing section 34 that is connected to the tool member 29 via a fillet 35. The fillet 35 extends along a strip of the otherwise cylindrical generated surface of the bearing pin 31 and extends along the entire axial length therefor. In addition, the bearing pin 31 may be joined to the actuating member 30, i.e., made in one piece, in particular along the end side. The bearing pin 31 can be axially inserted into the bearing bushing 23 (FIG. 5). This bearing bushing 23 has an opening 36 having a width 36a that is smaller than the diameter of the bearing section 34 but greater than the thickness of the fillet 35 measured in the same direction. This slit-like region of the bearing bushing 23 terminates in a cylindrical section 45 having a diameter that is minimally greater than the diameter of the bearing section 34. As a result of this, a desired pivoting movability of the jaw support 46 of the first jaw 16 on the socket part 18 is given. The maximum pivot angle is large enough that the tissue receiving range between the two jaws 16, 17 is sufficient for opening and closing. For purposes of assembling and disassembling, the jaws 16, 17 can also be pivoted away from each other at an even greater opening angle.

The jaw support 46 of the second jaw 17 is configured in the same manner in order to interact with the first bearing bushing 22. As is obvious from FIG. 5, the slit 24 is arranged between the two bearing bushings 22, 23 in such a manner that said slit extends between the two hinges.

Transverse interlocking means 37 are provided for laterally securing the jaw supports 46 of the jaws 16, 17 against each other, i.e., axially securing said supports relative to the bearing pin 31. For example, said interlocking means may be provided by complementary structures formed on the jaw supports 46 of the jaws 16, 17. For example, adjacent the bearing pin 31, offset laterally toward the center of the tool member 29, a projection may be provided on the jaw support 46, said projection having the shape of a rib 38, for example. For example, the rib 38 may curve at a constant radius relative to an axis 39 located between the hinge axes 27, 28. The rib 38 extends in circumferential direction U (FIG. 4) relative to this axis 39. Adjacent the rib 38 may be provided a recess having the shape of a pocket 40, for example, that extends in the same circumferential direction and is open toward the bearing pin 31. If a complementary rib of the jaw support 46 of the second jaw 17 comes into engagement with this pocket 40, this other rib is trapped between the rib 38 obvious from FIG. 4 and a cheek 41 and is thus secured in transverse direction. The pocket 40 is formed between the rib 38 and the cheek 41.

For mounting the two jaw supports 46 of the jaws 16, 17 to the socket part 18, the respective bearing pins 31 of the jaw supports 46 of the jaws 16, 17 that are spread far apart from each other are inserted into the bearing bushings 22, 23. They are then moved somewhat toward each other so that the respective rib 38 engages in its associate pocket 40 provided in the opposite jaw support 46. As soon as this is done, the jaws 16, 17 are secured against each other and can no longer fall off the socket part 18. It is sufficient if a rib 38 is formed on one jaw support 46 of the first jaw 17 and the pocket 40 is formed on the jaw support 46 of the second jaw 17. However, it is of advantage if each of the two jaw supports 46 of the first and the second jaws 16, 17 is provided with the rib 38 and the pocket 40.

Fastened to the jaw supports 46 of the jaws 16, 17, in particular their tool members 29, are the electrode units 42 obvious from FIG. 2, said units potentially comprising a central knife guide groove 43. With the jaws 16, 17 closed, said guide is in alignment with the slit 24. A distally advanced knife 25 that is precisely guided by the slit 24 can now be advanced in the knife guide groove 43 from the proximal to the distal end of the electrode units 42.

As shown by FIG. 6, the grasping range F for the tissue between the two jaws 16, 17 enlarges by the range FE, due to the spaced apart hinge axes 27, 28. The range FE is shown hatched in FIG. 6. The hinge axes 27, 28 that are arranged at a distance from the longitudinal axis L of the instrument cause the opening angle W of the tissue contact region of the jaws 16, 17 to be flatter compared to a tissue contact region of two jaws having hinge axes arranged on the longitudinal axis L of the instrument. The steeper opening angle W' is shown between two jaws 16' and 17' in FIG. 6. It can be clearly recognized that the relocation of the hinge axes 27, 28 away from the longitudinal axis L exhibiting the flatter opening angle W provides an additional range FE for tissue grasping.

The scissors-like closing of two jaws when tissue is being grasped has the effect that the tissue is clamped with greater force in the proximal grasping region than the tissue in the distal grasping region of the jaws. The reason for this is that, with the jaws opened, the distance between the jaws in the proximal grasping region is smaller than in the distal grasping region. Due to the relocation of the hinge axes 27, 28 away from the longitudinal axis L of the instrument 10 as described hereinabove, the opening angle W of the jaws 16, 17 becomes flatter. This directly affects the clamping force on the tissue. A homogeneous closing behavior of the jaws 16, 17 is the result because, due to the flatter opening angle W, the distance between the two jaws 16, 17 is increased in the proximal grasping region. This more homogeneous closing behavior of the jaws 16, 17 reduces the influence of the position in between the jaws 16, 17 where the tissue is being grasped, i.e., with respect to the clamping force.

A hinge axis 28 of a jaw support 46 being at a distance from the longitudinal axis L makes possible the arrangement of the actuating pin 33 in the available design space at a large distance in Z-direction of the hinge axis 27, 28. FIG. 6 shows the hinge axis 28 above the longitudinal axis L and the actuating pins 33$a$ associated with this hinge axis 28. Via the pull-push means, the pull-push force F1 oriented in the direction of the longitudinal axis L is made to act—preferably by means of a connecting member—in a force component F2 on the actuating pin 33. As a result of this a torque M about the hinge axis 28 is created, said torque acting on the jaw 16. Due to this torque M the tissue held between the two jaws 16, 17 is held strongly and securely. This increases the quality and reproduceability of tissue sealing. The greater the distance in Z-direction is between the hinge axis 28 and the actuating pin 33, the greater is the proportion of the force component F2 relevant to the torque M. If the push-pull force F1 has a linear component acting only on the actuating pin 33 and if the actuating pin 33 and the hinge axis 28 are on a common axis, no torque M about the hinge axis is generated. The effect of the distance in Z-direction between the hinge axis 28 and the actuating pin 33$a$ applies correspondingly to the hinge axis 27 and the actuating pin 33$b$.

The so far described instrument 10 operates as follows:

By means of not specifically illustrated pull-push means and a gear mechanism, the user can move the jaws 16, 17 toward each other and away from each other by moving the control lever 14. He now grasps, between the two jaws 16, 17, for example, a tissue bundle—that may also comprise vessels—that is to be coagulated or sealed and then to be severed, and clamps said bundle in place between the electrode units 42 by closing the jaws 16, 17. By means of a not specifically shown switch, he can now activate the electrode units 42 of the jaws 16, 17. They are connected by not specifically illustrated lines that extend through the shaft 12 and a line 44 leading away from the housing 11 to an electrical device, for example a generator. The generator may output, for example, an HF current or an HF voltage to the electrode units 42. The tissue grasped between the electrode units 42 is coagulated, desiccated and sealed as a result of this. Once this has been done, an actuating element can be activated to advance the knife 25 in distal direction where it is precisely guided thanks to the slit 24 and the knife guide groove 43. The frontal cutting edge of the knife 25 severs the coagulated and sealed tissue and can then be retracted.

The instrument 10 may be designed as a disposable instrument. It is also possible to make only parts of said instrument disposable, for example the tool 15 and/or the shaft 12. Owing to its simple design, the tool may also be made so as to be a sterilizable and reusable instrument, as required.

An instrument 10 having a tool 15 of a particularly simple design comprises jaw supports 46 of a first and a second jaw 16, 17, said jaws being supported by spaced-apart hinges on a shared socket part 18. The hinge axes 27, 28 of the hinges are oriented parallel relative to each other and are at a distance from each other. A slit 24 for precisely guiding a knife 25 may be provided between the two. The jaw supports 46 of the jaws 16, 17 are guided in their own hinges with minimal play and hence in a precise manner. They are held against each other by transverse interlocking means 37, thereby ensuring a simple assembly and precise guiding.

LIST OF REFERENCE SIGNS

10 Instrument
11 Housing
12 Shaft
13 Handle
14 Control lever
15 Tool
16, 16' First jaw
17, 17' Second jaw 18 Socket part
19 Distal support section of 18
20 Extension
21 Detent
22 First bearing bushing
23 Second bearing bushing
24 Slit
25 Knife
26 Groove for the stretch-resistant support of electrical lines
27, 28 Hinge axes
29 Tool member
30 Actuating member
31 Bearing pin
32 Window
33, 33a, 33b Actuating pins
34 Bearing section
35 Fillet
36 Opening
36a Width of 36
37 Transverse interlock means
38 Rib, projection
39 Axis
40 Pocket, recess
41 Cheek
42 Electrode units
43 Knife guide groove
44 Line
45 Cylindrical section
46 Jaw support
+X Direction transverse to the shaft 12
−X Opposite direction transverse to the shaft 12
U Circumferential direction to the axis 39
F Grasping range
FE Additional grasping range
W, W' Opening angle between the two jaws
M Torque about the hinge axis
F1 Pull-push force
F2 Force component for torque M
Z Direction perpendicular to the longitudinal axis L
L Longitudinal axis of the instrument

What is claimed is:

1. Surgical instrument (10), for tissue coagulation and vessel sealing, comprising:
  a tool (15) having two jaws (16, 17) that are supported on a socket part (18) so as to be pivotable about two different hinge axes (27, 28) toward each other and away from each other, wherein the hinge axes (27, 28):
    are defined by two spaced apart hinges, and
    are aligned parallel to each other;
  wherein individual ones of the two hinges comprises:
    a bearing pin (31) having a cylindrical bearing section (34) and a fillet (35) extending radially away from said bearing section, and
    a bearing bushing (22, 23) having an opening (36);
  wherein the opening (36) of the bearing bushing (23) has a width (36a) that is smaller than a diameter of the bearing section (34) and greater than a thickness of the fillet (35).

2. Surgical instrument as in claim 1, wherein the socket part (18) has a slit (24) for a knife, said slit being located between the hinge axes (27, 28).

3. Surgical instrument as in claim 1, wherein the bearing pin (31) is seamlessly connected to an actuating member (30) of the jaw (16, 17) on one end side.

4. Surgical instrument as in claim 1 wherein the bearing pin (31) is provided on the jaw (16) and on the bearing bushing (23) in the socket part (18).

5. Surgical instrument as in claim 1, wherein the socket part (18) is made of plastic material.

6. Surgical instrument as in claim 1, wherein the bearing bushings (22, 23) of the two hinges are oriented parallel to each other and are frontally open in opposite directions (+X, −X).

7. Surgical instrument as in claim 1, wherein at least one of the jaws (16, 17) comprises a jaw support (46).

8. Surgical instrument as in claim 1, wherein the two jaws (16, 17) comprise mutually engaging transverse interlocking means (37).

9. Surgical instrument as in claim 8, wherein the transverse interlocking means (37) comprise at least one projection (38) on a first jaw (16), said projection being configured so as to extend into a recess (40) of the second jaw (17).

10. Surgical instrument as in claim 9, wherein the projection (38) is a rib (38) extending on the jaw (16) relative to an axis (39) in circumferential direction (U).

11. Surgical instrument as in claim 10, wherein the recess is a pocket (40) provided on the jaw (16) in the circumferential direction (U).

12. Surgical instrument as in claim 11, wherein the pocket (40) and the rib (38) are laterally offset against each other.

13. Surgical instrument as in claim 11, wherein the pocket (40) and the rib (38) are offset against each other in the circumferential direction (U).

14. A method for operating a surgical instrument (10) for tissue coagulation and vessel sealing, the method comprising:
  moving two jaws (16, 17) supported on a socket part (18) of a tool (15) toward each other and away from each other pivotally about respective and different hinge axes (27, 28) that are spaced apart and aligned parallel to each other, wherein the different hinge axes are defined by two spaced apart hinges, wherein individual ones of the two hinges comprises:
    a bearing pin (31) having a cylindrical bearing section (34) and a fillet (35) extending radially away from said bearing section, and
    a bearing bushing (22, 23) having an opening (36);
  wherein the opening (36) of the bearing bushing (23) has a width (36a) that is smaller than a diameter of the bearing section (34) and greater than a thickness of the fillet (35).

15. The method of claim 14 further comprising sliding a knife through a slit located between the hinge axes.

* * * * *